United States Patent [19]
Mather et al.

[11] Patent Number: 5,143,078
[45] Date of Patent: Sep. 1, 1992

[54] RESPIRATION RATE MONITOR

[75] Inventors: Bruce C. Mather; Dean C. Winter, both of San Antonio, Tex.

[73] Assignee: Colin Electronics Co., Ltd., Japan

[21] Appl. No.: 414,658

[22] Filed: Sep. 29, 1989

Related U.S. Application Data

[63] Continuation of Ser. No. 81,250, Aug. 4, 1987, abandoned.

[51] Int. Cl.$^5$ .................................................. A61B 5/08
[52] U.S. Cl. ...................................... 128/716; 128/671
[58] Field of Search ........................ 128/716, 763, 671

[56]  References Cited

U.S. PATENT DOCUMENTS

| | | | |
|---|---|---|---|
| 4,306,567 | 12/1981 | Krasner | 128/721 |
| 4,686,999 | 8/1987 | Snyder et al. | 128/716 |
| 4,694,837 | 9/1987 | Blakeley et al. | 128/696 |

OTHER PUBLICATIONS

Zarra, Conf.: Procedd. 7th New Eng. Bioeng. Conf., Troy, N.Y., Nov. 22-23, 1979.

*Primary Examiner*—Kyle L. Howell
*Attorney, Agent, or Firm*—Oliff & Berridge

[57] ABSTRACT

A monitoring system for providing an accurate indication of a patient's respiration rate. The system is effective in eliminating or significantly reducing the effects of heart sounds and ambient noise. The system comprises means for obtaining a first signal waveform containing components corresponding to the patient's breath sounds, as well as components corresponding to heart sounds and ambient noise. The signal is passed through a digital bandpass filter having a passband selected to remove heart sounds and ambient noise to produce a second waveform. From the second waveform the total energy is computed of a portion of the signal within a moving window of predetermined length. The resulting energy envelope signal is smoothed and then high-pass filtered by removing the average DC value of the signal over a predetermined preceding time interval. Respiration is detected by identifying significant, positive-going zero crossings of the resulting signal through a band about zero. The zero-band threshold used to obtain this waveform can be controlled by the operator or pre-set for a particular sensitivity.

6 Claims, 4 Drawing Sheets

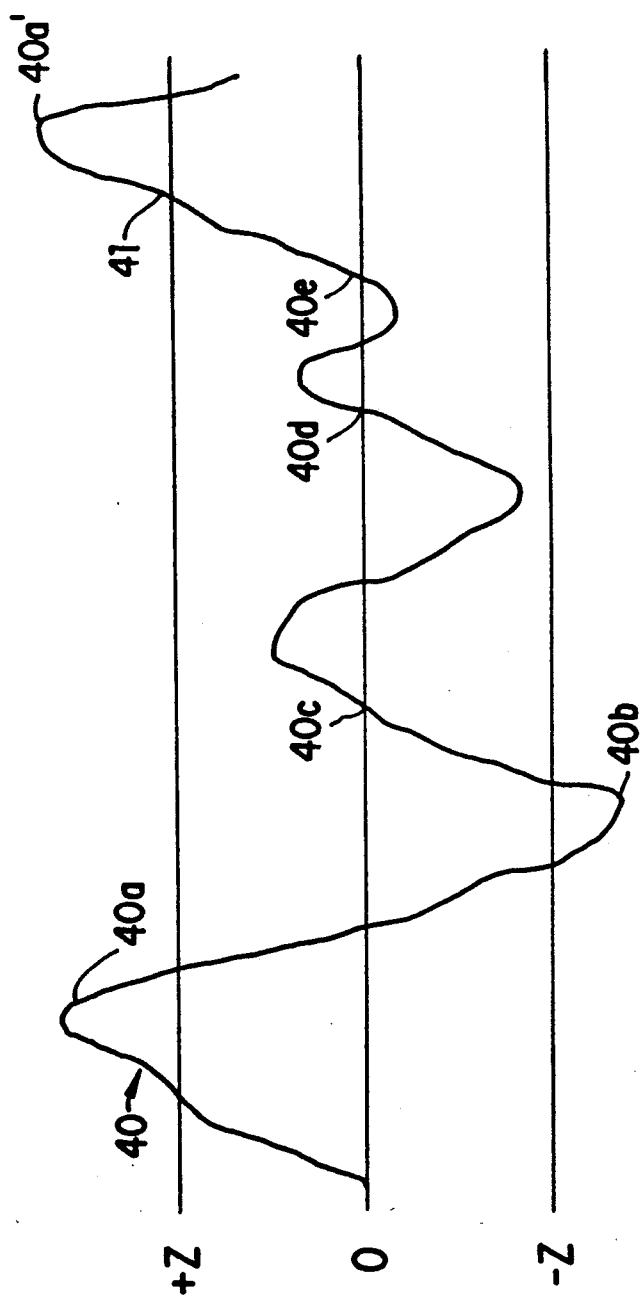

RESPIRATION RATE MONITOR

This is a continuation of co-pending application Ser. No. 07/081,250 filed on Aug. 4, 1987, now abandoned.

FIELD OF THE INVENTION

The present invention relates generally to the field of physiological monitoring and more particularly to respiration rate detection and monitoring. Specifically, the present invention provides an accurate respiration rate monitor which is resistant to the effects of ambient noise and interference.

BACKGROUND

It is often desirable for a physician to be able to monitor a patient's respiration rate over relatively long periods of time. Accurate monitoring of respiration rate is especially important in the case of infants suspected to be susceptible to crib death or sudden infant death syndrome (SIDS). Children believed to be at a high risk of SIDS are often monitored with various types of respiration monitoring devices which are designed to detect apnea, or the cessation of breathing.

One of the most common commercially available apnea monitors is based on an impedance pneumograph. This device operates by creating an alternating current signal between electrodes mounted on the thorax. Respiration is detected by measuring a change in the impedance between the electrode as the chest expands. Specifically, this device is based on a correlation between the impedance measured between the electrodes and the respiratory tidal volume in the non-moving subject, whereby changes in subject position affect the amplitude of the detected signal. These types of devices, however, have been found to be inaccurate because certain movements can occur in a non-breathing subject which produce a signal very similar to a respiratory waveform.

Another electromechanical respiration monitoring device is based on a magnetometer which measures respiration by correlating the distance between electrodes mounted on the chest and back of the patient. Although this device can be used to measure respiration, it is extremely sensitive to motion artifacts and to the erroneous detection of respiration due to spurious signals. In addition, both the magnetometer and the impedance type monitor often give erroneous indications of respiration because the chest cavity will expand when the patient attempts to breathe even though there may be an obstruction which prevents the actual flow of air.

In recent years, there has been considerable interest in the development of a respiration monitor capable of measuring respiration rate from a patient's breath sounds. One of the major problems that has prevented the development of a respiration rate monitor based on breath sounds, however, is that of identifying breath sounds in the presence of other, unrelated sounds. These other sounds may be generated by the subject (e.g., talking, snoring, abdominal sounds, muscle sounds and heart sounds) or external to the subject (e.g., machine noise, talking by other people, radio and television noise, footsteps and doors closing). Subject-generated noise, the main source of which is heart sounds, is difficult to control or monitor independent of breath sound noise. The respiration rate monitor provided by the present invention overcomes these difficulties, as discussed in greater detail below.

SUMMARY OF THE INVENTION

The present invention provides a system for determining respiration rate in the presence of noise signals such as those discussed above. The system comprises means for obtaining a first waveform containing components corresponding to the patient's breath sounds, as well as components corresponding to heart sounds and ambient noise. This first waveform signal is passed through a digital bandpass filter having a passband selected to remove heart sounds and ambient noise to produce a second waveform. From the second waveform the total energy is computed of a portion of the waveform within a moving window of predetermined length. The resulting energy envelope signal is then smoothed with a 0.5 second moving average (a low-pass filter) and then high-pass filtered by removing the average DC value of the data over a preceding period of time of predetermined length. Respiration is detected by identifying significant, positive-going zero crossings of the resulting signal through a band about zero. The zero-band threshold used to obtain this waveform can be controlled by the operator or pre-set for a particular sensitivity. The signals which satisfy the criteria of the banded zero-crossing detector produce a series of markers indicating respiration breath sound events. The series of markers can then be processed to calculate respiration rate. The processing algorithm implemented by the invention system provides an accurate indication of the patient's respiration rate and is effective in eliminating or significantly reducing the effects of heart sounds and ambient noise.

BRIEF DESCRIPTION OF THE DRAWINGS

FIG. 4a is a graphical illustration of the operation of the banded zero-crossing detector used to detect respiration rate in the monitoring system of the present invention.

DETAILED DESCRIPTION OF THE PREFERRED EMBODIMENT

Figure 1:
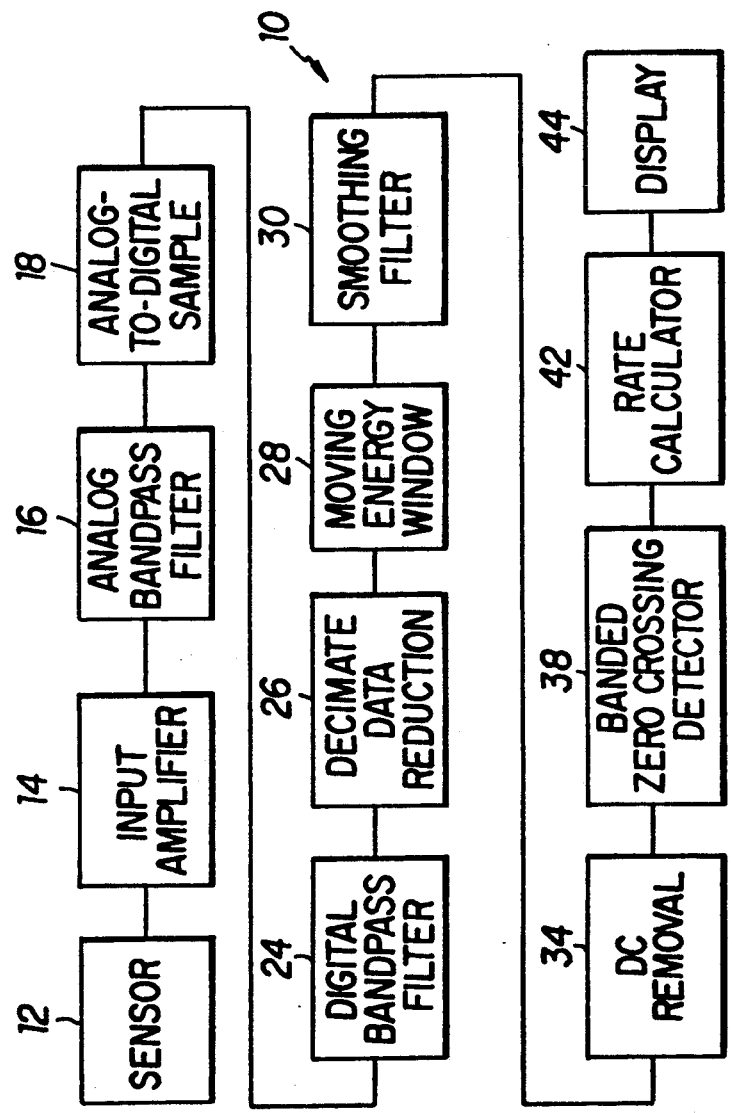
FIG. 1 is a block diagram generally showing the preferred embodiment of the present invention.
Figure 2:
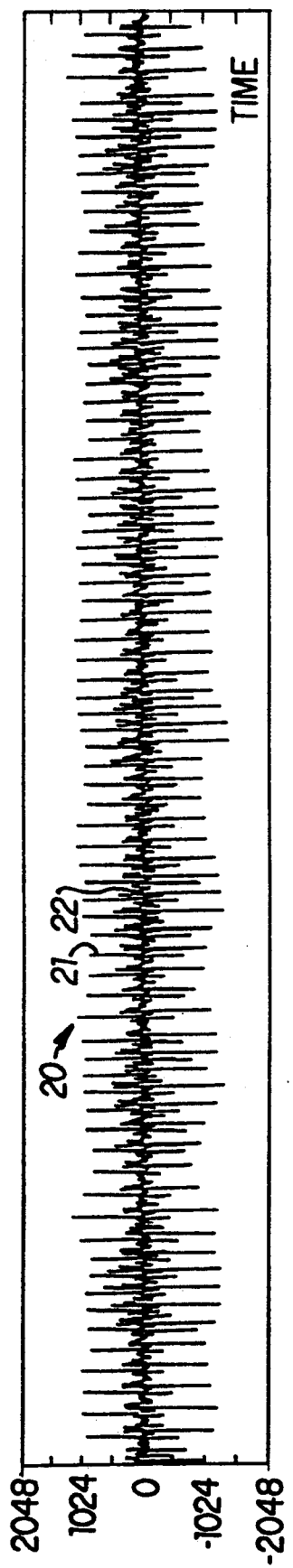
FIG. 2 is a graphical representation of anti-aliased breath sound data obtained from a biomedical transducer.

The respiration rate provided by the present invention is based on the detection of breath sounds in the presence of other biological signals and ambient noise. Referring to the drawings in more detail, and to FIG. 1 in particular, the preferred embodiment of the respiration rate monitor of the present invention is shown. The breath sounds are detected by an appropriate biological sensor 12, such as a microphone, which is sensitive to acoustical energy in the bandwidths of interest. A wide variety of sensors can be employed for detection of the breath sounds, including those comprising air-coupled stethoscope microphones and piezoelectric devices. The sensor 12 produces an electrical output signal which corresponds to a waveform comprising a component related to the patient's breath sounds, a component related to the patient's heart sounds, and a plurality of components related to other biological functions and ambient noise. The output signal produced by the sensor 12 is amplified by the input amplifier 14 and filtered in the analog bandpass filter 16. In the preferred embodiment of the invention system, the analog bandpass filter 16 has a passband of between 0.1 Hz and 1000 Hz. The analog output signal produced by the bandpass filter is digitized by the analog-to-digital (A/D) sample module 18 to produce a digital output signal. In the preferred embodiment, the A/D sampling is at a rate of approximately 4000 hertz. A typical anti-aliased output signal 20 produced by the A/D sampling module is illustrated in FIG. 2. As can be seen in this figure, the output signal comprises a plurality of high amplitude peaks 21 which represent acoustic signals produced by the patient's heart, a plurality of lower amplitude signals 22 which represent the breath sounds produced by the patient, and a plurality of other signal components produced by biological and environmental factors.

In order to calculate respiration rate from the waveform 20 shown in FIG. 2, it is necessary to amplify the signals 22 corresponding to the patient's breath sounds and to filter out the heart rate signals and other signal components contained in the waveform. For signal processing of the type needed to detect breath sounds, it is preferable to filter the signal in the digital domain rather than the analog domain in order to achieve a nearly ideal passband. Furthermore it is desirable to sample the signal at a high frequency rate. The digitized signal shown in FIG. 2 is filtered in a digital bandpass filter 24 which, in the preferred embodiment, has a passband of 300 to 600 Hz. This filter effectively removes the heart sounds from the waveform shown in FIG. 2. The resultant output signal is then processed by a decimate data reduction module 26 which provides a 2-to-1 reduction in the number of filtered data samples. This signal, which can be represented as x(n), is illustrated by the waveform 27 shown in FIG. 3. As can be seen, the signals corresponding to the heart sounds 21 have been removed from the waveform and the signals corresponding to the breath sounds 22 have been amplified.

Figure 3:
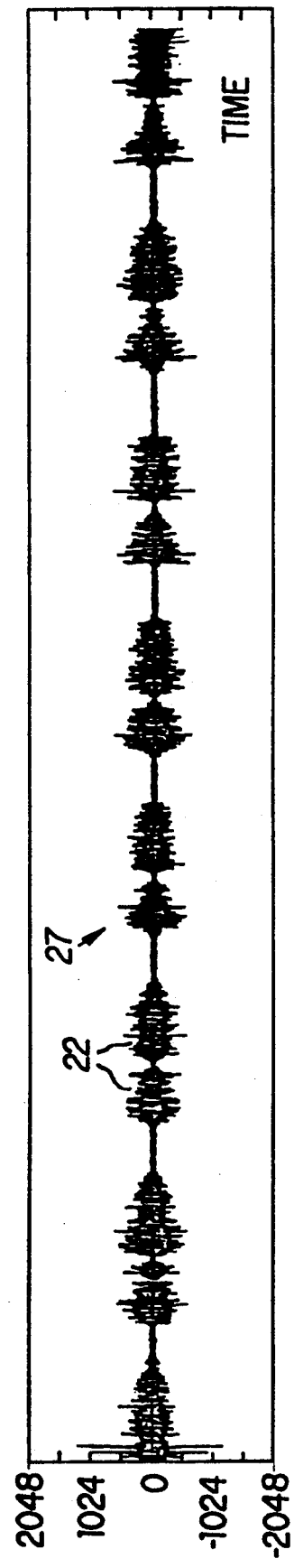
FIG. 3 is a graphical representation of the breath sound data shown in FIG. 1, with the signals relating to heart sounds filtered therefrom.

In order to identify breath sounds, it is necessary to identify large "chunks" of continuous energy in the waveform 27 shown in FIG. 3. This is accomplished by processing the waveform shown in FIG. 3 in a moving energy window 28 which calculates the root-mean-square energy of the signal in a time window of predetermined width. Specifically, the energy of the signal within the window is calculated using the following formula:

$$y(n) = \sqrt{\left[\sum_{j=0}^{N} x^2(n-j)\right]/N} , \quad \text{Eq. (1)}$$

where n and j are indices of the samples. The width of the window in Eq. (1) is determined by the variable N. In the preferred embodiment, the time window has a width of 0.125 seconds.

The resulting energy signal y(n) produced by the moving energy window 28 is smoothed in a smoothing filter 30 which calculates the average value of the waveform over a previous time period of predetermined length. The smoothing filter used in the preferred embodiment calculates the energy over the previous 0.5 second using the following moving average formula:

$$y'(n) = \left[\sum_{j=0}^{M} x(n-j)\right]/M \quad \text{Eq. (2)}$$

The time period over which the smoothing occurs is determined by the variable M in Eq. (2). This smoothing of the signal has essentially the same effect as a low pass filter.

The resulting smoothed output signal is then processed by a DC removal module 34 which removes the average value of the data over a predetermined preceding time interval. In the preferred embodiment, the DC removal module is adapted to remove the average value of the previous four seconds of data. The DC removal is accomplished using the following formula:

$$y''(n) = y'(n) - \left[\sum_{j=0}^{L} y'(n-j)\right]/L \quad \text{Eq. (3)}$$

The DC removal module essentially acts as a high-pass filter with the value of L in Eq. (3) determining the cutoff frequency of the filter. The removal of the DC component of the signal creates a AC coupled, bi-polar signal which can be further processed in the banded zero-crossing detector, discussed below.

Figure 4:
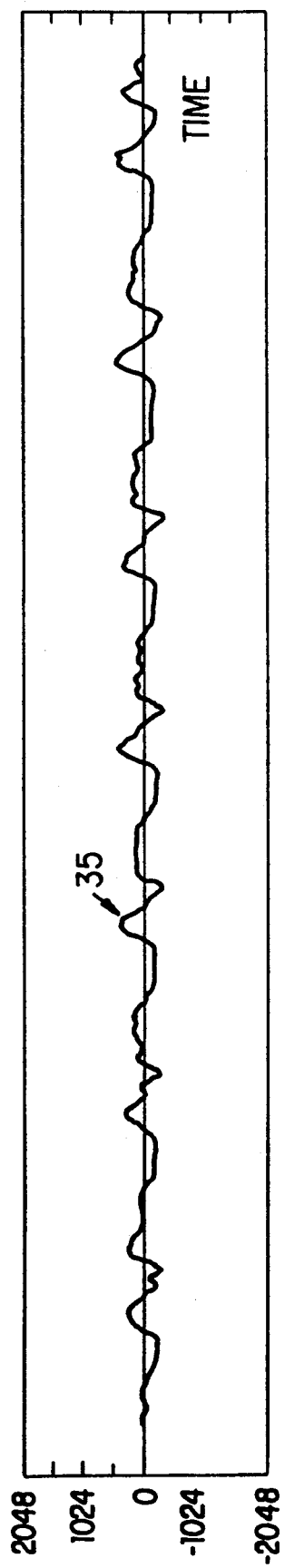
FIG. 4 is a graphical representation of the energy envelope of the waveform shown in FIG. 3 after being smoothed and high pass filtered.

The resulting waveform 35 produced by this series of processing steps is shown in FIG. 4. As can be seen, the resulting waveform comprises a plurality of peaks and troughs. The peaks in FIG. 4 correspond to either an inspiration event or an expiration breath sound event. In order to calculate respiration rate, the waveform 35 shown in FIG. 4 is processed by a banded zero-crossing detector 38. Operation of the banded zero-crossing detector can be seen by referring to the waveform 40 shown in FIG. 4a. The waveform comprises a plurality of peaks and troughs such as those shown in FIG. 4. Each of the peaks 40a and 40a' represents either an inspiration or an expiration breath sound. The trough 40b represents an absence of breath sound. In order to calculate a respiration rate from the signal 40, it is necessary to locate "significant, positive-going" zero crossings in the waveform. The level of significance for determining zero crossings can be set by defining an amplitude band between +Z and −Z about the zero axis. In the preferred embodiment, the value of Z is set at 50 samples. For a point to qualify as a significant zero crossing, it must occur at a point in time after the waveform 40 has passed into the band +Z, −Z, exited through the lower boundary of the band and re-entered the band to exit through the upper boundary. For example, in FIG. 4a, none of the points 40c, 40d, or 40e would qualify as a significant zero crossing. However, point 41 would qualify as a significant zero crossing since it meets the criteria defined above.

Figure 5:
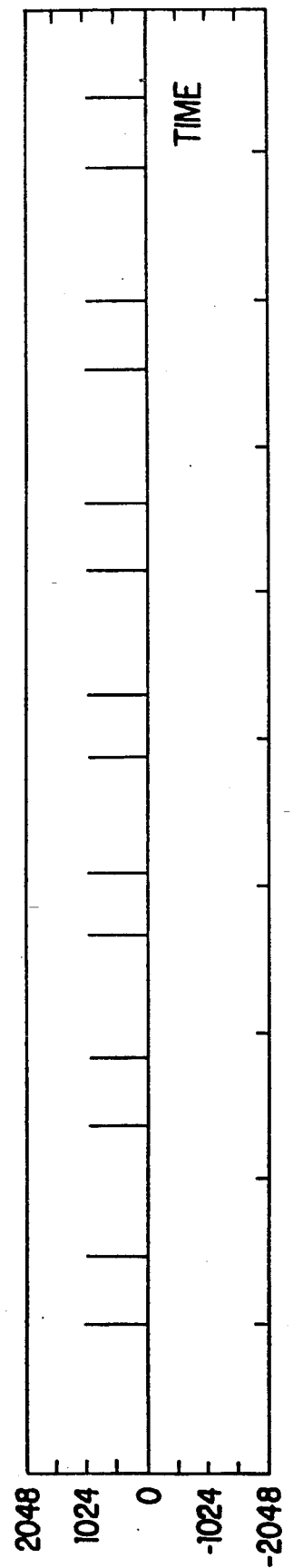
FIG. 5 is a graphical representation of the respiration rate data obtained from the waveform shown in FIG. 4 after being processed by the banded zero crossing detector.

The banded zero-crossing detector 38 processes the waveform shown in FIG. 4 to produce a series of markers indicating the occurrence of inspiration and expiration events. These markers are shown in FIG. 5. The marked event times are further processed by a rate calculator 42 to provide an indication of the respiration rate which is then displayed on the display 44. The processing routine employed in the rate calculator 42 can be calculated by a number of different techniques which are known in the art.

Experimental results have shown that the respiration described herein provides an effective means for determining respiration rate from a patient's breath sound. In particular, the system provided by the present invention is very effective in determining respiration rate in the presence of ambient noise and interference.

While the respiration rate monitor of the present invention has been described in connection with the preferred embodiment, it is not intended to limit the invention to the specific form set forth herein, but on the contrary, it is intended to cover such alternatives, modifications and equivalents as may be included within the scope and spirit of the invention as defined by the appended claims.

We claim:

1. A system for monitoring the respiration rate of a patient, comprising:
    means for detecting acoustical energy generated by said patient and for producing a first output signal in response thereto, said output signal comprising a component corresponding to breath sounds, a component corresponding to heart sounds and a component corresponding to ambient noise;
    means for filtering said first output signal to remove said components corresponding to said heart sounds and ambient noise and for producing a second output signal corresponding only to said breath sounds;
    means for producing an AC coupled energy signal corresponding to the breath sound energy level of said second output signal; and
    means for identifying significant positive-going zero crossings in said AC coupled energy signal within a band of predetermined width and for correlating said significant zero crossings with the respiration rate of said patient.

2. A system in accordance with claim 1, wherein said means for filtering said first output signal comprises a bandpass filter having a passband of 300 to 600 Hz.

3. A system in accordance with claim 2, wherein said means for producing said AC coupled energy signal comprises means for calculating the root-mean-square energy of said second output signal.

4. A method for determining respiration rate of a patient, comprising the steps of:
    detecting acoustical energy generated by said patient and producing a first output signal in response thereto, said output signal comprising a component corresponding to breath sounds, a component corresponding to heart sounds and a component corresponding to ambient noise;
    filtering said first output signal to remove said components corresponding to said heart sounds and ambient noise and producing a second output signal corresponding only to said breath sounds;
    producing an AC coupled energy signal corresponding to the breath sound energy level of said second output signal; and
    identifying significant positive-going zero crossings in said AC coupled energy signal within a band of predetermined width and correlating said significant zero crossings with the respiration rate of said patient.

5. The method according to claim 4, wherein said means for filtering said first output signal comprises a bandpass filter having a passband of 300 to 600 Hz.

6. The method according to claim 5, wherein said means for producing said AC coupled energy signal comprises means for calculating the root-mean-square energy of said second output signal.

* * * * *